(12) United States Patent
Yu et al.

(10) Patent No.: US 10,059,995 B2
(45) Date of Patent: Aug. 28, 2018

(54) METHOD FOR DETERMINING $P_1/P_2$ BLOOD TYPE AND DETECTION KIT THEREOF

(71) Applicant: National Taiwan University, Taipei (TW)

(72) Inventors: Lung-Chih Yu, Taipei (TW); Marie Lin, New Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 15/841,854

(22) Filed: Dec. 14, 2017

(65) Prior Publication Data
US 2018/0135125 A1    May 17, 2018

Related U.S. Application Data

(62) Division of application No. 14/505,493, filed on Oct. 2, 2014.

(30) Foreign Application Priority Data

Oct. 14, 2013 (TW) .............................. 10-2136933

(51) Int. Cl.
*C12Q 1/68*    (2018.01)
*C12Q 1/6881*  (2018.01)

(52) U.S. Cl.
CPC ..... *C12Q 1/6881* (2013.01); *C12Q 2600/156* (2013.01)

(58) Field of Classification Search
None
See application file for complete search history.

(56) References Cited

U.S. PATENT DOCUMENTS

2002/0090623 A1    7/2002  Smith et al.
2012/0065079 A1*   3/2012  Olsson ................. C12Q 1/6881
                                                          506/2

OTHER PUBLICATIONS

GenBank (see the dbSNP entry for rs5751348 first added with build 114 on Apr. 28, 2003) (Year: 2003).*
Mummidi et al (Journal of Biological Chemistry 2000 vol. 275 No. 25 pp. 18946-18961) (Year: 2000).*

* cited by examiner

*Primary Examiner* — Amanda Haney
(74) *Attorney, Agent, or Firm* — Mintz Levin Cohn Ferris Glovsky and Popeo, P.C.; Peter F. Corless

(57) ABSTRACT

The present invention provides a method for determining $P_1/P_2$ blood type, including steps of providing a biological sample of a subject, detecting a genotype for single nucleotide polymorphism rs2143918 or rs5751348 in A4GALT gene of the biological sample and determining a phenotype of the subject based on the genotype. Further, the present invention also provides a kit for determining $P_1/P_2$ blood type, including a primer pair for detecting a genotype for single nucleotide polymorphisms rs2143918 or rs5751348 in A4GALT gene of a nucleic acid sample of a subject.

2 Claims, 2 Drawing Sheets

Specification includes a Sequence Listing.

FIG. 1

| Family | Phenotype | SNP | | | | | | | | | | |
|---|---|---|---|---|---|---|---|---|---|---|---|---|
| | | 1 | 2 | 3 | 4 | 5 | 6 | 7 | 8 | 9 | 10 | 11 |
| Father | $P_2$ | ■ | ■ | ■ | | | | | | | | |
| | | | | | | | | | | | | |
| Mother | $P_1$ | ■ | ■ | ■ | ■ | ■ | ■ | ■ | ■ | ■ | ■ | ■ |
| | | | | | | | | | | | | |
| M3 | $P_1$ | ■ | ■ | ■ | ■ | ■ | ■ | ■ | ■ | ■ | ■ | ■ |
| | | ■ | ■ | ■ | | | | | | | | |
| brothers | $P_2$ | ■ | ■ | ■ | | | | | | | | |

SEQUENCE LISTING

<160> NUMBER OF SEQ ID NOS: 113

<210> SEQ ID NO 1
<211> LENGTH: 20
<212> TYPE: DNA
<213> ORGANISM: Artificial Sequence
<220> FEATURE:
<223> OTHER INFORMATION: Forward primer

<400> SEQUENCE: 1
aagtgcacct cctctcactc                           20

<210> SEQ ID NO 2
<211> LENGTH: 18
<212> TYPE: DNA
<213> ORGANISM: Artificial Sequence
<220> FEATURE:
<223> OTHER INFORMATION: Reverse primer

<400> SEQUENCE: 2
tctagctttc ccatcagc                             18

<210> SEQ ID NO 3
<211> LENGTH: 18
<212> TYPE: DNA
<213> ORGANISM: Artificial Sequence
<220> FEATURE:
<223> OTHER INFORMATION: Forward primer 2

<400> SEQUENCE: 3
tcacgagcat tcctcatc                             18

<210> SEQ ID NO 4
<211> LENGTH: 20
<212> TYPE: DNA
<213> ORGANISM: Artificial Sequence
<220> FEATURE:
<223> OTHER INFORMATION: Reverse primer 2

<400> SEQUENCE: 4
ctcctctcta tctctctgtc                           20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gtgcatgcct gtaatcacag                           20

<210> SEQ ID NO 6

```
<211> LENGTH: 20
<212> TYPE: DNA
<213> ORGANISM: Artificial Sequence
<220> FEATURE:
<223> OTHER INFORMATION: primer

<400> SEQUENCE: 6
gtgtcacagt gactgctgtg                                               20

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7
attgacaagg gcgagccac                                                19

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
aagcaaacac tcctccctcc                                               20

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9
atgggtggag tggaaagtg                                                19

<210> SEQ ID NO 10
<211> LENGTH: 19
<212> TYPE: DNA
<213> ORGANISM: Artificial Sequence
<220> FEATURE:
<223> OTHER INFORMATION: primer

<400> SEQUENCE: 10
aagacagagt ctccctgtc                                                19

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
tgtggctctg actactgag                                                19

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
```
acacacctag aagccatcc                                                19

<210> SEQ ID NO 13
<211> LENGTH: 29
<212> TYPE: DNA
<213> ORGANISM: Artificial Sequence
<220> FEATURE:
<223> OTHER INFORMATION: primer

<400> SEQUENCE: 13
gcagtggctc ccttgacata agtaactcc                                     29

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
ttatgtcaag ggagccactg                                               20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
gtcaacatct agaccactgc                                               20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
accagaaagt tggagctagg                                               20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
aactggagct ggtcatctgg                                               20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
atctgctttg gagcatgggc                                               20

<210> SEQ ID NO 19
<211> LENGTH: 20
<212> TYPE: DNA

```
<213> ORGANISM: Artificial Sequence
<220> FEATURE:
<223> OTHER INFORMATION: primer

<400> SEQUENCE: 19
ctgggattac aggcgtgagc                                                 20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
cagctccagt ttactgatgg                                                 20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
gtcaggctgg tcttgatcac                                                 20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
caagaccagc ctgaccaacg                                                 20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
ggttgagcac acaggctctg                                                 20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
ctctcagagc ctgtgtgctc                                                 20

<210> SEQ ID NO 25
<211> LENGTH: 19
<212> TYPE: DNA
<213> ORGANISM: Artificial Sequence
<220> FEATURE:
<223> OTHER INFORMATION: primer

<400> SEQUENCE: 25
agccccagca gcctttgag                                                  19
```

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
aatgatccta ctgcctcagc                                              20

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
tattcaaggc aggccagcac                                              20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
tcgctctgtc gccatactgg                                              20

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
ctcagcctcc cacagtgtgg                                              20

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
gacggagtct cactctgtcg                                              20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
gttgccttct agtctctgag                                              20

<210> SEQ ID NO 32
<211> LENGTH: 21
<212> TYPE: DNA
<213> ORGANISM: Artificial Sequence
<220> FEATURE:

<223> OTHER INFORMATION: primer

<400> SEQUENCE: 32
gaagagactc actctgttac c                                              21

<210> SEQ ID NO 33
<211> LENGTH: 29
<212> TYPE: DNA
<213> ORGANISM: Artificial Sequence
<220> FEATURE:
<223> OTHER INFORMATION: primer

<400> SEQUENCE: 33
ttagccatgg ttgtgcatgc ctgtagtcc                                      29

<210> SEQ ID NO 34
<211> LENGTH: 29
<212> TYPE: DNA
<213> ORGANISM: Artificial Sequence
<220> FEATURE:
<223> OTHER INFORMATION: primer

<400> SEQUENCE: 34
aggccaggca agcactcacg cctgtaatc                                      29

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
atctcaggtg acctgcttgc                                                20

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
gggtgacttc ttgagtgctg                                                20

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
acccattgag tgccaggctc                                                20

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
accgtgctaa gggcattgcc                                                20

<210> SEQ ID NO 39
<211> LENGTH: 30
<212> TYPE: DNA
<213> ORGANISM: Artificial Sequence
<220> FEATURE:
<223> OTHER INFORMATION: primer

<400> SEQUENCE: 39
caccaggact gtgacatgct ggaaacatgg                    30

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
ctgcctcgaa cccggcttct                              20

<210> SEQ ID NO 41
<211> LENGTH: 29
<212> TYPE: DNA
<213> ORGANISM: Artificial Sequence
<220> FEATURE:
<223> OTHER INFORMATION: primer

<400> SEQUENCE: 41
ggagaagccg ggttcgaggc aggctctgc                    29

<210> SEQ ID NO 42
<211> LENGTH: 31
<212> TYPE: DNA
<213> ORGANISM: Artificial Sequence
<220> FEATURE:
<223> OTHER INFORMATION: primer

<400> SEQUENCE: 42
gctttaaccc actcagggcc agaggctcag c                 31

<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
gtgaggattt ggacctgccc                              20

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
actacagtga gctgccacag                              20

<210> SEQ ID NO 45
<211> LENGTH: 20
<212> TYPE: DNA
<213> ORGANISM: Artificial Sequence
<220> FEATURE:
<223> OTHER INFORMATION: primer

```
<400> SEQUENCE: 45
caacgtcgag tgattgttcc                                                    20

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
ggttgcagct atggaaacac                                                    20

<210> SEQ ID NO 47
<211> LENGTH: 20
<212> TYPE: DNA
<213> ORGANISM: Artificial Sequence
<220> FEATURE:
<223> OTHER INFORMATION: primer

<400> SEQUENCE: 47
atagcagagt gcggatggag                                                    20

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
tgtagtctca aactgctagg                                                    20

<210> SEQ ID NO 49
<211> LENGTH: 19
<212> TYPE: DNA
<213> ORGANISM: Artificial Sequence
<220> FEATURE:
<223> OTHER INFORMATION: primer

<400> SEQUENCE: 49
caatcctgct ccacactgg                                                     19

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
gctgctaggt taatgggtcc                                                    20

<210> SEQ ID NO 51
<211> LENGTH: 20
<212> TYPE: DNA
<213> ORGANISM: Artificial Sequence
<220> FEATURE:
<223> OTHER INFORMATION: primer

<400> SEQUENCE: 51
ttcaggaagc acctgctagg                                                    20

<210> SEQ ID NO 52
<211> LENGTH: 20
```

```
<212> TYPE: DNA
<213> ORGANISM: Artificial Sequence
<220> FEATURE:
<223> OTHER INFORMATION: primer

<400> SEQUENCE: 52
aagtgcacct cctctcactc                                               20

<210> SEQ ID NO 53
<211> LENGTH: 20
<212> TYPE: DNA
<213> ORGANISM: Artificial Sequence
<220> FEATURE:
<223> OTHER INFORMATION: primer

<400> SEQUENCE: 53
ctcactgcac tctctgcctc                                               20

<210> SEQ ID NO 54
<211> LENGTH: 18
<212> TYPE: DNA
<213> ORGANISM: Artificial Sequence
<220> FEATURE:
<223> OTHER INFORMATION: primer

<400> SEQUENCE: 54
tctagctttc ccatcagc                                                 18

<210> SEQ ID NO 55
<211> LENGTH: 20
<212> TYPE: DNA
<213> ORGANISM: Artificial Sequence
<220> FEATURE:
<223> OTHER INFORMATION: primer

<400> SEQUENCE: 55
gacagagaga tagagaggag                                               20

<210> SEQ ID NO 56
<211> LENGTH: 19
<212> TYPE: DNA
<213> ORGANISM: Artificial Sequence
<220> FEATURE:
<223> OTHER INFORMATION: primer

<400> SEQUENCE: 56
tatgtggaca ctggtctgg                                                19

<210> SEQ ID NO 57
<211> LENGTH: 20
<212> TYPE: DNA
<213> ORGANISM: Artificial Sequence
<220> FEATURE:
<223> OTHER INFORMATION: primer

<400> SEQUENCE: 57
ccttccagac cagtgtccac                                               20

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
```
aacagagcat ggtggctgag                                               20

<210> SEQ ID NO 59
<211> LENGTH: 18
<212> TYPE: DNA
<213> ORGANISM: Artificial Sequence
<220> FEATURE:
<223> OTHER INFORMATION: primer

<400> SEQUENCE: 59
ccctgatcat ctgtgacc                                                 18

<210> SEQ ID NO 60
<211> LENGTH: 18
<212> TYPE: DNA
<213> ORGANISM: Artificial Sequence
<220> FEATURE:
<223> OTHER INFORMATION: primer

<400> SEQUENCE: 60
aaaagctcac tgtcaggc                                                 18

<210> SEQ ID NO 61
<211> LENGTH: 20
<212> TYPE: DNA
<213> ORGANISM: Artificial Sequence
<220> FEATURE:
<223> OTHER INFORMATION: primer

<400> SEQUENCE: 61
ctattaaacc acacagctcc                                               20

<210> SEQ ID NO 62
<211> LENGTH: 18
<212> TYPE: DNA
<213> ORGANISM: Artificial Sequence
<220> FEATURE:
<223> OTHER INFORMATION: primer

<400> SEQUENCE: 62
attagcaggg aatggtgg                                                 18

<210> SEQ ID NO 63
<211> LENGTH: 21
<212> TYPE: DNA
<213> ORGANISM: Artificial Sequence
<220> FEATURE:
<223> OTHER INFORMATION: primer

<400> SEQUENCE: 63
gagtgcactg gtgcaatcat g                                             21

<210> SEQ ID NO 64
<211> LENGTH: 21
<212> TYPE: DNA
<213> ORGANISM: Artificial Sequence
<220> FEATURE:
<223> OTHER INFORMATION: primer

<400> SEQUENCE: 64
cttcatacca taaattccaa g                                             21

<210> SEQ ID NO 65
<211> LENGTH: 20
<212> TYPE: DNA
<213> ORGANISM: Artificial Sequence

```
<220> FEATURE:
<223> OTHER INFORMATION: primer

<400> SEQUENCE: 65
gtccttcagc agctctcaag                                               20

<210> SEQ ID NO 66
<211> LENGTH: 19
<212> TYPE: DNA
<213> ORGANISM: Artificial Sequence
<220> FEATURE:
<223> OTHER INFORMATION: primer

<400> SEQUENCE: 66
tggctccctc ctgtaattc                                                19

<210> SEQ ID NO 67
<211> LENGTH: 18
<212> TYPE: DNA
<213> ORGANISM: Artificial Sequence
<220> FEATURE:
<223> OTHER INFORMATION: primer

<400> SEQUENCE: 67
ggagtgcggt ggtatgag                                                 18

<210> SEQ ID NO 68
<211> LENGTH: 20
<212> TYPE: DNA
<213> ORGANISM: Artificial Sequence
<220> FEATURE:
<223> OTHER INFORMATION: primer

<400> SEQUENCE: 68
atctggcaaa accccacctc                                               20

<210> SEQ ID NO 69
<211> LENGTH: 21
<212> TYPE: DNA
<213> ORGANISM: Artificial Sequence
<220> FEATURE:
<223> OTHER INFORMATION: primer

<400> SEQUENCE: 69
cctaacctca ggtgatccac c                                             21

<210> SEQ ID NO 70
<211> LENGTH: 19
<212> TYPE: DNA
<213> ORGANISM: Artificial Sequence
<220> FEATURE:
<223> OTHER INFORMATION: primer

<400> SEQUENCE: 70
ctcccccagc atcacctac                                                19

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71 cccctctca ggcagtatcc                                                20
```

```
<210> SEQ ID NO 72
<211> LENGTH: 18
<212> TYPE: DNA
<213> ORGANISM: Artificial Sequence
<220> FEATURE:
<223> OTHER INFORMATION: primer

<400> SEQUENCE: 72
caccttcgct ctggacac                                          18

<210> SEQ ID NO 73
<211> LENGTH: 20
<212> TYPE: DNA
<213> ORGANISM: Artificial Sequence
<220> FEATURE:
<223> OTHER INFORMATION: primer

<400> SEQUENCE: 73
ttgcatctct gggatctctg                                        20

<210> SEQ ID NO 74
<211> LENGTH: 20
<212> TYPE: DNA
<213> ORGANISM: Artificial Sequence
<220> FEATURE:
<223> OTHER INFORMATION: primer

<400> SEQUENCE: 74
agtacctgac tacttgccag                                        20

<210> SEQ ID NO 75
<211> LENGTH: 18
<212> TYPE: DNA
<213> ORGANISM: Artificial Sequence
<220> FEATURE:
<223> OTHER INFORMATION: primer

<400> SEQUENCE: 75
tgagaagcca gccccacc                                          18

<210> SEQ ID NO 76
<211> LENGTH: 20
<212> TYPE: DNA
<213> ORGANISM: Artificial Sequence
<220> FEATURE:
<223> OTHER INFORMATION: primer

<400> SEQUENCE: 76
ccgagtctcg ctctgttgcc                                        20

<210> SEQ ID NO 77
<211> LENGTH: 19
<212> TYPE: DNA
<213> ORGANISM: Artificial Sequence
<220> FEATURE:
<223> OTHER INFORMATION: primer

<400> SEQUENCE: 77
gaggttgtag tgagccaag                                         19

<210> SEQ ID NO 78
<211> LENGTH: 19
<212> TYPE: DNA
<213> ORGANISM: Artificial Sequence
<220> FEATURE:
<223> OTHER INFORMATION: primer
```

```
<400> SEQUENCE: 78
ctgtgagcaa acaggcatg                                                19

<210> SEQ ID NO 79
<211> LENGTH: 20
<212> TYPE: DNA
<213> ORGANISM: Artificial Sequence
<220> FEATURE:
<223> OTHER INFORMATION: primer

<400> SEQUENCE: 79
tgtggtagga tctgtgctgg                                               20

<210> SEQ ID NO 80
<211> LENGTH: 20
<212> TYPE: DNA
<213> ORGANISM: Artificial Sequence
<220> FEATURE:
<223> OTHER INFORMATION: primer

<400> SEQUENCE: 80
tagctactca ggaggctgag                                               20

<210> SEQ ID NO 81
<211> LENGTH: 20
<212> TYPE: DNA
<213> ORGANISM: Artificial Sequence
<220> FEATURE:
<223> OTHER INFORMATION: primer

<400> SEQUENCE: 81
tgcagcaagc caagatggtg                                               20

<210> SEQ ID NO 82
<211> LENGTH: 20
<212> TYPE: DNA
<213> ORGANISM: Artificial Sequence
<220> FEATURE:
<223> OTHER INFORMATION: primer

<400> SEQUENCE: 82
agcctcctga gtagctaggg                                               20

<210> SEQ ID NO 83
<211> LENGTH: 20
<212> TYPE: DNA
<213> ORGANISM: Artificial Sequence
<220> FEATURE:
<223> OTHER INFORMATION: primer

<400> SEQUENCE: 83
catcttggct tgctgcagcc                                               20

<210> SEQ ID NO 84
<211> LENGTH: 20
<212> TYPE: DNA
<213> ORGANISM: Artificial Sequence
<220> FEATURE:
<223> OTHER INFORMATION: primer

<400> SEQUENCE: 84
acagtttcat acctgggcac                                               20

<210> SEQ ID NO 85
```

```
<211> LENGTH: 20
<212> TYPE: DNA
<213> ORGANISM: Artificial Sequence
<220> FEATURE:
<223> OTHER INFORMATION: primer

<400> SEQUENCE: 85
gctcaagcaa tctggctgcc                                                     20

<210> SEQ ID NO 86
<211> LENGTH: 20
<212> TYPE: DNA
<213> ORGANISM: Artificial Sequence
<220> FEATURE:
<223> OTHER INFORMATION: primer

<400> SEQUENCE: 86
acacagaagc caggaaccag                                                     20

<210> SEQ ID NO 87
<211> LENGTH: 20
<212> TYPE: DNA
<213> ORGANISM: Artificial Sequence
<220> FEATURE:
<223> OTHER INFORMATION: primer

<400> SEQUENCE: 87
tggtggtggc agcatctgtg                                                     20

<210> SEQ ID NO 88
<211> LENGTH: 20
<212> TYPE: DNA
<213> ORGANISM: Artificial Sequence
<220> FEATURE:
<223> OTHER INFORMATION: primer

<400> SEQUENCE: 88
ggcaggtgga tcacttgagg                                                     20

<210> SEQ ID NO 89
<211> LENGTH: 20
<212> TYPE: DNA
<213> ORGANISM: Artificial Sequence
<220> FEATURE:
<223> OTHER INFORMATION: primer

<400> SEQUENCE: 89
gattacagtt gtgccccacc                                                     20

<210> SEQ ID NO 90
<211> LENGTH: 20
<212> TYPE: DNA
<213> ORGANISM: Artificial Sequence
<220> FEATURE:
<223> OTHER INFORMATION: primer

<400> SEQUENCE: 90
caagtacatg atcctcccac                                                     20

<210> SEQ ID NO 91
<211> LENGTH: 20
<212> TYPE: DNA
<213> ORGANISM: Artificial Sequence
<220> FEATURE:
<223> OTHER INFORMATION: primer

<400> SEQUENCE: 91
```

```
tgggagccta ggaattcaag                                              20

<210> SEQ ID NO 92
<211> LENGTH: 19
<212> TYPE: DNA
<213> ORGANISM: Artificial Sequence
<220> FEATURE:
<223> OTHER INFORMATION: primer

<400> SEQUENCE: 92
ggatcccaga agacatagc                                               19

<210> SEQ ID NO 93
<211> LENGTH: 23
<212> TYPE: DNA
<213> ORGANISM: Artificial Sequence
<220> FEATURE:
<223> OTHER INFORMATION: primer

<400> SEQUENCE: 93
gtagattagc tatgtcttct ggg                                          23

<210> SEQ ID NO 94
<211> LENGTH: 20
<212> TYPE: DNA
<213> ORGANISM: Artificial Sequence
<220> FEATURE:
<223> OTHER INFORMATION: primer

<400> SEQUENCE: 94
atcgcgccat tgcattctag                                              20

<210> SEQ ID NO 95
<211> LENGTH: 20
<212> TYPE: DNA
<213> ORGANISM: Artificial Sequence
<220> FEATURE:
<223> OTHER INFORMATION: primer

<400> SEQUENCE: 95
ctggcactgc aggtacacac                                              20

<210> SEQ ID NO 96
<211> LENGTH: 20
<212> TYPE: DNA
<213> ORGANISM: Artificial Sequence
<220> FEATURE:
<223> OTHER INFORMATION: primer

<400> SEQUENCE: 96
acacagaaac atggctggtc                                              20

<210> SEQ ID NO 97
<211> LENGTH: 20
<212> TYPE: DNA
<213> ORGANISM: Artificial Sequence
<220> FEATURE:
<223> OTHER INFORMATION: primer

<400> SEQUENCE: 97
attgttacat acactggtgg                                              20

<210> SEQ ID NO 98
<211> LENGTH: 20
<212> TYPE: DNA
```

```
<213> ORGANISM: Artificial Sequence
<220> FEATURE:
<223> OTHER INFORMATION: primer

<400> SEQUENCE: 98
actctctacc ctagtgatag                                              20

<210> SEQ ID NO 99
<211> LENGTH: 20
<212> TYPE: DNA
<213> ORGANISM: Artificial Sequence
<220> FEATURE:
<223> OTHER INFORMATION: primer

<400> SEQUENCE: 99
gcacagtatc tatcactagg                                              20

<210> SEQ ID NO 100
<211> LENGTH: 20
<212> TYPE: DNA
<213> ORGANISM: Artificial Sequence
<220> FEATURE:
<223> OTHER INFORMATION: primer

<400> SEQUENCE: 100
gagacatacc ttaaacgaag                                              20

<210> SEQ ID NO 101
<211> LENGTH: 18
<212> TYPE: DNA
<213> ORGANISM: Artificial Sequence
<220> FEATURE:
<223> OTHER INFORMATION: primer

<400> SEQUENCE: 101
atcctggcta acacggtg                                                18

<210> SEQ ID NO 102
<211> LENGTH: 19
<212> TYPE: DNA
<213> ORGANISM: Artificial Sequence
<220> FEATURE:
<223> OTHER INFORMATION: primer

<400> SEQUENCE: 102
tcagcctccc gagtaactg                                               19

<210> SEQ ID NO 103
<211> LENGTH: 20
<212> TYPE: DNA
<213> ORGANISM: Artificial Sequence
<220> FEATURE:
<223> OTHER INFORMATION: primer

<400> SEQUENCE: 103
tcgcttgaac ctgggaagtg                                              20

<210> SEQ ID NO 104
<211> LENGTH: 19
<212> TYPE: DNA
<213> ORGANISM: Artificial Sequence
<220> FEATURE:
<223> OTHER INFORMATION: primer

<400> SEQUENCE: 104
cctcggccta ttaaagtgc                                               19
```

<210> SEQ ID NO 105
<211> LENGTH: 20
<212> TYPE: DNA
<213> ORGANISM: Artificial Sequence
<220> FEATURE:
<223> OTHER INFORMATION: primer

<400> SEQUENCE: 105
tgaggagcac aaatactcgc                                                   20

<210> SEQ ID NO 106
<211> LENGTH: 20
<212> TYPE: DNA
<213> ORGANISM: Artificial Sequence
<220> FEATURE:
<223> OTHER INFORMATION: primer

<400> SEQUENCE: 106
agcgagtatt tgtgctcctc                                                   20

<210> SEQ ID NO 107
<211> LENGTH: 18
<212> TYPE: DNA
<213> ORGANISM: Artificial Sequence
<220> FEATURE:
<223> OTHER INFORMATION: primer

<400> SEQUENCE: 107 aagacccag aaaaggcc                                                      18

<210> SEQ ID NO 108
<211> LENGTH: 20
<212> TYPE: DNA
<213> ORGANISM: Artificial Sequence
<220> FEATURE:
<223> OTHER INFORMATION: primer

<400> SEQUENCE: 108
aaaggctccc tcctctgttg                                                   20

<210> SEQ ID NO 109
<211> LENGTH: 20
<212> TYPE: DNA
<213> ORGANISM: Artificial Sequence
<220> FEATURE:
<223> OTHER INFORMATION: primer

<400> SEQUENCE: 109
gaagccagga atcaagcagg                                                   20

<210> SEQ ID NO 110
<211> LENGTH: 20
<212> TYPE: DNA
<213> ORGANISM: Artificial Sequence
<220> FEATURE:
<223> OTHER INFORMATION: primer

<400> SEQUENCE: 110
tctgtttgta acgtccaccc                                                   20

<210> SEQ ID NO 111
<211> LENGTH: 20
<212> TYPE: DNA
<213> ORGANISM: Artificial Sequence
<220> FEATURE:

```
<223> OTHER INFORMATION: primer

<400> SEQUENCE: 111
ccttcactgc tttgtccatc                                              20

<210> SEQ ID NO 112
<211> LENGTH: 20
<212> TYPE: DNA
<213> ORGANISM: Artificial Sequence
<220> FEATURE:
<223> OTHER INFORMATION: primer

<400> SEQUENCE: 112
gcagggtttg gaagctctgg                                              20

<210> SEQ ID NO 113
<211> LENGTH: 20
<212> TYPE: DNA
<213> ORGANISM: Artificial Sequence
<220> FEATURE:
<223> OTHER INFORMATION: primer

<400> SEQUENCE: 113
tgtgcccggc ctgcaataag                                              20
```

| | | | | | | | | | | | | |

METHOD FOR DETERMINING $P_1/P_2$ BLOOD TYPE AND DETECTION KIT THEREOF

CROSS-REFERENCE(S) TO RELATED APPLICATION

The present application is a divisional application of U.S. patent application Ser. No. 14/505,493 filed Oct. 2, 2014, which claims priority of Taiwanese Patent Application Number 10-2136933 filed on Oct. 14, 2013, the entire contents of which application are incorporated herein for all purposes by this reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 048293-446D01U_SeqListing.txt, date recorded: Nov. 23, 2016, size: 20,610 bytes.)

BACKGROUND OF THE INVENTION

1. Field of the Invention

The present invention relates to a method for determining $P_1/P_2$ blood type and a detection kit thereof, and more particularly to a method with a single nucleotide polymorphism for determining $P_1/P_2$ blood type and a detection kit thereof.

2. Description of Related Art

In 1927, Austrian Biologist Karl Landsteiner and American immunologist Philip Levine discovered a new antigen from the rabbits transfused human blood during research on hemolytic disease of the newborns. These antigens can cause clotting of the red blood cells in some people while other groups of people are unaffected. They namely these two blood types as $P_1$ (+) and $P_1$ (−), later, the P1 (+)- and P1 (−) type are referred to as P1 and P2 type. This $P_1/P_2$ blood type belongs to the third system among the present 33 human blood type.

$P_1/P_2$ blood type is a system composed of glycolipid antigens; however the molecular genetic basis is still not clear. $P_1$ blood type and $P_2$ blood type are correlated to $P_1$ and $P^k$ blood antigens expressed on the red blood cell. The $P_1$ and $P^k$ are carbohydrate antigens and are synthesized via different biosynthetic routes, starting from a common glycosphingolipid precursor, lactosylceramide. The $P_1$ and $P^k$ antigens are determined by the enzymatic activity of α-1, 4-galactosyltransferase (hereinafter referred to as A4GALT). $P_1/P_2$ blood type is a common phenotypic polymorphism and the distribution of which varies among different human populations. The frequency of $P_1$ type in Caucasians and Africans are 80% and 90-95%, respectively, while the frequency of $P_1$ type is relatively low in Asians. The frequency of $P_1$ blood type is about 30% to 40% in Taiwan.

Using DNA genotype as a method for detecting blood type will be a trend in the future. For instance, Progenika Biopharma, S.A. (Spain) has developed a blood chip and such blood chip contains various genotype variations of different blood type. However, in the past, the molecular genetic mechanism of $P_1/P_2$ blood type has not been verified, such that the current DNA test including Progenika blood chip could not contain this common $P_1/P_2$ blood type polymorphism to perform DNA analysis. Therefore, there still is a need for determining the $P_1/P_2$ blood type.

Thuresson et al. (Thuresson B, Westman J S, Olsson M L, Identification of a novel A4GALT exon reveals the genetic basis of the $P_1/P_2$ histo-blood groups. Blood. 2011; 117(2): 678-687.) has reported the association between SNP rs8138197 and $P_1/P_2$ phenotypes, and proposed a novel molecular model of the formation of $P_1/P_2$ blood group.

The present invention utilizes a genetic association study among different ethnic populations to prove single nucleotide polymorphism (hereinafter referred to as SNP) rs2143918 and rs5751348 in A4GALT gene are completely associated with $P_1/P_2$ blood type. The result of the present invention provides the molecular genetic mechanism of $P_1/P_2$ blood type and further provides a marker for determining $P_1/P_2$ blood type by using the genotypes of SNPs rs2143918 and rs5751348.

SUMMARY OF THE INVENTION

The present invention aims to conduct a pilot investigation among four ethnic groups, and the results from analysis of $P_1$ type of Africans and a Taiwanese family pedigree labeled M3 reveals that a genotype of SNP rs8138197 is not associated with $P_1/P_2$ blood type.

The present invention provides a method for determining $P_1/P_2$ blood type, comprising steps of: providing a biological sample of a subject; detecting a genotype for a single nucleotide polymorphism at rs2143918 or rs5751348 in A4GALT gene of the biological sample; and determining a phenotype of the subject based on the genotype.

In one embodiment of the present invention, the genotype of the single nucleotide polymorphism at rs2143918 is selected from the group consisting of T/T, T/G and G/G In one embodiment of the present invention, T/T or T/G genotype of the single nucleotide polymorphism at rs2143918 represents $P_1$ phenotype in the subject.

In one embodiment of the present invention, G/G genotype of the single nucleotide polymorphism at rs2143918 represents $P_2$ phenotype in the subject.

In one embodiment of the present invention, the genotype of the single nucleotide polymorphism at rs5751348 is selected from the group consisting of G/G, G/T and T/T.

In one embodiment of the present invention, G/G or G/T genotype of the single nucleotide polymorphism at rs5751348 represents $P_1$ phenotype in the subject.

In one embodiment of the present invention, T/T genotype of the single nucleotide polymorphism at rs5751348 represents $P_2$ phenotype in the subject.

In one embodiment of the present invention, the biological samples are blood or saliva.

In one embodiment of the present invention, a nucleic acid in the biological sample is determined by polymerase chain reaction (hereinafter referred to as PCR).

In one embodiment of the present invention, a primer pair of SEQ ID Nos: 1 and 2 are used in the PCR for determining the nucleic acids of the biological samples.

In one embodiment of the present invention, a primer pair of SEQ ID Nos: 3 and 4 are used in the PCR for determining the nucleic acids of the biological samples.

The present invention also provides a detection kit for determining $P_1/P_2$ blood type, comprising: a primer pair for determining a genotype of a single nucleotide polymorphism at rs2143918 or rs5751348 of A4GALT gene in a nucleic acid sample of a subject.

In one embodiment of the present invention, the primer pair has sequences of SEQ ID Nos: 1 and 2.

In one embodiment of the present invention, the primer pair has sequences of SEQ ID Nos: 3 and 4.

In one embodiment of the present invention, the genotype of the single nucleotide polymorphism at rs2143918 is selected from the group consisting of T/T, T/G and G/G In one embodiment of the present invention, T/T or T/G genotype of the single nucleotide polymorphism at rs2143918 represents $P_1$ phenotype in the subject.

In one embodiment of the present invention, G/G genotype of the single nucleotide polymorphism at rs2143918 represents $P_2$ phenotype in the subject.

In one embodiment of the present invention, the genotype of the single nucleotide polymorphism at rs5751348 is selected from the group consisting of G/G, G/T and T/T.

In one embodiment of the present invention, G/G or G/T genotype of the single nucleotide polymorphism at rs5751348 represents $P_1$ phenotype in the subject.

In one embodiment of the present invention, T/T genotype of the single nucleotide polymorphism at rs5751348 represents $P_2$ phenotype in the subject.

BRIEF DESCRIPTION OF THE DRAWINGS

FIG. 1 shows distributions of the most likely haplotype pairs in $P_1/P_2$ individuals across 4 ethnic populations; and FIG. 2 shows $P_1/P_2$ phenotypes and the most likely haplotype pairs of M3 family.

DETAILED DESCRIPTION OF THE PREFERRED EMBODIMENTS

The following specific examples are used for illustrating the present invention. A person skilled in the art can easily conceive the other advantages and effects of the present invention. The present invention can also be implemented by different specific cases be enacted or application, the details of the instructions can also be based on different perspectives and applications in various modifications and changes do not depart from the spirit of the creation.

The present invention provides a method for determining $P_1/P_2$ blood type, comprising steps of providing a biological sample of a subject; determining a genotype for a single nucleotide polymorphism (SNP) of A4GALT gene from the biological samples, wherein the SNP is located at SNP rs2143918 or SNP rs5751348; and discriminating the subject has $P_1$ or $P_2$ phenotype according to the genotype of SNP rs2143918 or SNP rs5751348.

The present invention also provides a kit for determining $P_1/P_2$ blood type, comprising a PCR primer pair, which is used to amplify nucleic acid fragments of a single nucleotide polymorphism of A4GALT gene by using the nucleic acid of the subject to be determined as a template. The single nucleotide polymorphism is located at SNP rs2143918 or SNP rs5751348, wherein the PCR primer pair can perform an extension reaction of the primer so as to determine the genotype of SNP rs2143918 or SNP rs5751348 and discriminate the subject has $P_1$ or $P_2$ phenotype.

Example 1: Method for Determining $P_1/P_2$ Phenotype

1. Sample Preparation and $P_1/P_2$ Phenotype

A total of 338 non-related subjects across four ethnic populations, including 227 Taiwanese, 32 Indians, 46 Caucasians, and 33 Africans (Blacks, including 2 African-Americans) were enrolled in the present invention. Peripheral blood samples were collected from each subject. The genomic DNAs were purified from the peripheral blood samples using QIAamp DNA Blood Mini Kit (Qiagen GmbH, Hilden, Germany), and then the $P_1/P_2$ phenotype of each sample was determined by a standard hemagglutination test using monoclonal anti-P1 reagent (Immucor Inc., Houston, Tex.).

2. Analysis of the Single Nucleotide Polymorphism

57 DNA fragments were amplified by polymerase chain reaction (hereinafter referred to as PCR), and these encompassed all SNP sites distribute from −7.0 kb to +17.3 kb of the A4GALT gene. The sequences of PCR primer pairs locations thereof are listed in Table 1. Then, the nucleotides at the SNP sites were determined by direct sequencing the amplified DNA fragments using Sanger's method.

TABLE 1

| PCR primers for SNP analysis | | | |
|---|---|---|---|
| primer | sequence(5' → 3') | location[a] | SEQ ID NO. |
| 930R | GTGCATGCCTGTAATCACAG | −7085 | 5 |
| 930F | GTGTCACAGTGACTGCTGTG | −6765 | 6 |
| 217F | ATTGACAAGGGCGAGCCAC | −6800 | 7 |
| 217R | AAGCAAACACTCCTCCCTCC | −6618 | 8 |
| 928R | ATGGGTGGAGTGGAAAGTG | −6564 | 9 |
| 928F | AAGACAGAGTCTCCCTGTC | −6236 | 10 |
| 931F | TGTGGCTCTGACTACTGAG | −713 | 11 |
| 931R | ACACCTAGAAGCCATCC | −5983 | 12 |
| 678F | GCAGTGGCTCCCTTGACATAAGTAACTCC | −5265 | 13 |
| 677R | TTATGTCAAGGGAGCCACTG | −5285 | 14 |
| 677F | GTCAACATCTAGACCACTGC | −4950 | 15 |
| 584F | ACCAGAAAGTTGGAGCTAGG | −5129 | 16 |

TABLE 1-continued

PCR primers for SNP analysis

| primer | sequence(5' → 3') | location[a] | SEQ ID NO. |
|---|---|---|---|
| 584R | AACTGGAGCTGGTCATCTGG | −4521 | 17 |
| 331R | ATCTGCTTTGGAGCATGGGC | −4834 | 18 |
| 331F | CTGGGATTACAGGCGTGAGC | −4437 | 19 |
| 853R | CAGCTCCAGTTTACTGATGG | −4532 | 20 |
| 853F | GTCAGGCTGGTCTTGATCAC | −4056 | 21 |
| 690F1 | CAAGACCAGCCTGACCAACG | −4070 | 22 |
| 690R2 | GGTTGAGCACACAGGCTCTG | −3480 | 23 |
| 628R2 | CTCTCAGAGCCTGTGTGCTC | −3503 | 24 |
| 628F1 | AGCCCCAGCAGCCTTTGAG | −3193 | 25 |
| 644F | AATGATCCTACTGCCTCAGC | −3078 | 26 |
| 676F | TATTCAAGGCAGGCCAGCAC | −2182 | 27 |
| 676R | TCGCTCTGTCGCCATACTGG | −2684 | 28 |
| 676F | TATTCAAGGCAGGCCAGCAC | −2182 | 27 |
| 795F | CTCAGCCTCCCACAGTGTGG | −1607 | 29 |
| 795R | GACGGAGTCTCACTCTGTCG | −2138 | 30 |
| 326R | GTTGCCTTCTAGTCTCTGAG | −1783 | 31 |
| 326F | GAAGAGACTCACTCTGTTACC | −1383 | 32 |
| 035R | TTAGCCATGGTTGTGCATGCCTGTAGTCC | −1524 | 33 |
| 035F | AGGCCAGGCAAGCACTCACGCCTGTAATC | −1056 | 34 |
| 369R | ATCTCAGGTGACCTGCTTGC | −1125 | 35 |
| 369F | GGGTGACTTCTTGAGTGCTG | −680 | 36 |
| 898R | ACCCATTGAGTGCCAGGCTC | −799 | 37 |
| 898F | ACCGTGCTAAGGGCATTGCC | −373 | 38 |
| A4GTFa | CACCAGGACTGTGACATGCTGGAAACATGG | −626 | 39 |
| PKRL | CTGCCTCGAACCCGGCTTCT | +430 | 40 |
| 469F3 | GGAGAAGCCGGGTTCGAGGCAGGCTCTGC | +409 | 41 |
| 469R4 | GCTTTAACCCACTCAGGGCCAGAGGCTCAGC | +939 | 42 |
| 845R | GTGAGGATTTGGACCTGCCC | +596 | 43 |
| 927F | ACTACAGTGAGCTGCCACAG | +1472 | 44 |
| 573R | CAACGTCGAGTGATTGTTCC | +1002 | 45 |
| 573F | GGTTGCAGCTATGGAAACAC | +1303 | 46 |
| 927R | ATAGCAGAGTGCGGATGGAG | +1188 | 47 |
| 927F | ACTACAGTGAGCTGCCACAG | +1472 | 44 |
| 672R | TGTAGTCTCAAACTGCTAGG | +1467 | 48 |
| 672F | CAATCCTGCTCCACACTGG | +1783 | 49 |
| 920R | GCTGCTAGGTTAATGGGTCC | +1710 | 50 |
| 920F | TTCAGGAAGCACCTGCTAGG | +2186 | 51 |
| 522R | AAGTGCACCTCCTCTCACTC | +1985 | 52 |

TABLE 1-continued

PCR primers for SNP analysis

| primer | sequence (5' → 3') | location[a] | SEQ ID NO. |
|---|---|---|---|
| 522F | CTCACTGCACTCTCTGCCTC | +2538 | 53 |
| 175F | TCTAGCTTTCCCATCAGC | +3239 | 54 |
| 926R | GACAGAGAGATAGAGAGGAG | +3132 | 55 |
| 926F | TATGTGGACACTGGTCTGG | +3800 | 56 |
| 991R | CCTTCCAGACCAGTGTCCAC | +3778 | 57 |
| 991F | AACAGAGCATGGTGGCTGAG | +4136 | 58 |
| 181R | CCCTGATCATCTGTGACC | +4018 | 59 |
| 181F | AAAGCTCACTGTCAGGC | +4501 | 60 |
| 181Fs | CTATTAAACCACACAGCTCC | +4462 | 61 |
| 860F | ATTAGCAGGGAATGGTGG | +5307 | 62 |
| 183F | GAGTGCACTGGTGCAATCATG | +5189 | 63 |
| 183R | CTTCATACCATAAATTCCAAG | +5674 | 64 |
| 894R | GTCCTTCAGCAGCTCTCAAG | +5750 | 65 |
| 892R | TGGCTCCCTCCTGTAATTC | +6553 | 66 |
| 176F | GGAGTGCGGTGGTATGAG | +6627 | 67 |
| 858R | ATCTGGCAAAACCCCACCTC | +7245 | 68 |
| 245F | CCTAACCTCAGGTGATCCACC | +7267 | 69 |
| 245R | CTCCCCCAGCATCACCTAC | +7915 | 70 |
| 718F | CCCCTTCTCAGGCAGTATCC | +7843 | 71 |
| 718R | CACCTTCGCTCTGGACAC | +8550 | 72 |
| 291F | TTGCATCTCTGGGATCTCTG | +8429 | 73 |
| 291R | AGTACCTGACTACTTGCCAG | +8760 | 74 |
| 888F | TGAGAAGCCAGCCCCACC | +8637 | 75 |
| 888R | CCGAGTCTCGCTCTGTTGCC | +9215 | 76 |
| 185F | GAGGTTGTAGTGAGCCAAG | +9153 | 77 |
| 185R | CTGTGAGCAAACAGGCATG | +9533 | 78 |
| 306F | TGTGGTAGGATCTGTGCTGG | +9272 | 79 |
| 306R | TAGCTACTCAGGAGGCTGAG | +9942 | 80 |
| 887R | TGCAGCAAGCCAAGATGGTG | +10216 | 81 |
| 887F | AGCCTCCTGAGTAGCTAGGG | +9926 | 82 |
| 081F | CATCTTGGCTTGCTGCAGCC | +10200 | 83 |
| 081R | ACAGTTTCATACCTGGGCAC | +10779 | 84 |
| 347R | GCTCAAGCAATCTGGCTGCC | +10368 | 85 |
| 347F | ACACAGAAGCCAGGAACCAG | +10825 | 86 |
| 793F | TGGTGGTGGCAGCATCTGTG | +10719 | 87 |
| 793R | GGCAGGTGGATCACTTGAGG | +11293 | 88 |
| 653F | GATTACAGTTGTGCCCCACC | +11179 | 89 |
| 479R | CAAGTACATGATCCTCCCAC | +11697 | 90 |

TABLE 1-continued

PCR primers for SNP analysis

| primer | sequence(5' → 3') | location[a] | SEQ ID NO. |
|---|---|---|---|
| 616F | TGGGAGCCTAGGAATTCAAG | +11563 | 91 |
| 616R | GGATCCCAGAAGACATAGC | +11988 | 92 |
| 993F | GTAGATTAGCTATGTCTTCTGGG | +11962 | 93 |
| 993R | ATCGCGCCATTGCATTCTAG | +12521 | 94 |
| 227F | CTGGCACTGCAGGTACACAC | +12422 | 95 |
| 227R | ACACAGAAACATGGCTGGTC | +13012 | 96 |
| 634F | ATTGTTACATACACTGGTGG | +13082 | 97 |
| 634R | ACTCTCTACCCTAGTGATAG | +13708 | 98 |
| 280F | GCACAGTATCTATCACTAGG | +13680 | 99 |
| 280R | GAGACATACCTTAAACGAAG | +14387 | 100 |
| 712R | ATCCTGGCTAACACGGTG | +14693 | 101 |
| 036F | TCAGCCTCCCGAGTAACTG | +14594 | 102 |
| 036R | TCGCTTGAACCTGGGAAGTG | +14884 | 103 |
| 903F | CCTCGGCCTATTAAAGTGC | +15079 | 104 |
| 903R | TGAGGAGCACAAATACTCGC | +15590 | 105 |
| 557F | AGCGAGTATTTGTGCTCCTC | +15570 | 106 |
| 557R | AAGACCCCAGAAAAGGCC | +15934 | 107 |
| 881F | AAAGGCTCCCTCCTCTGTTG | +15731 | 108 |
| 881R | GAAGCCAGGAATCAAGCAGG | +16230 | 109 |
| 436F | TCTGTTTGTAACGTCCACCC | +16177 | 110 |
| 436R | CCTTCACTGCTTTGTCCATC | +16889 | 111 |
| 193F | GCAGGGTTTGGAAGCTCTGG | +16787 | 112 |
| 193R | TGTGCCCGGCCTGCAATAAG | +17308 | 113 |

[a]Transcription initiation nucleotide of A4GALT exon 1 of RefSeq Transcript

3. Primer Pairs for Amplification and Identification of the Genotypes of Rs2143918 and rs5751348

The forward primer for amplification and identification the genotype of rs2143918 has the sequence of SEQ ID No. 1, while the reverse primer has the sequence of SEQ ID No. 2.

```
    AAGTGCACCTCCTCTCACTC    (SEQ ID NO. 1)
    TCTAGCTTTCCCATCAGC      (SEQ ID NO. 2)
```

The forward primer for amplification and identification the genotype of rs5751347 has the sequence of SEQ ID No. 3, while the reverse primer has the sequence of SEQ ID No. 4.

```
    TCACGAGCATTCCTCATC      (SEQ ID NO: 3)
    CTCCTCTCTATCTCTCTGTC    (SEQ ID NO: 4)
```

4. Result

1) A pilot investigation for identification of SNPs in A4GALT gene associated with the $P_1/P_2$ phenotype.

In order to explore the molecular genetic basis of the $P_1/P_2$ blood groups, the present invention conducted a pilot investigation, which involved the detailed and stepwise screening of SNPs in A4GALT gene from four Taiwanese with the $P_1$ phenotype and four Taiwanese with the $P_2$ phenotype. The screening of SNP started from the 5' promoter region and then extended stepwise to the 5' and 3' region of the gene to identify any polymorphic nucleotide positions that may be related to $P_1/P_2$ phenotypes. The PCR, which was used to amplify the DNA fragments encompassing each SNP in the A4GALT gene, has been recorded in the SNP database of the National Center for Biotechnology Information (NCBI). Eventually, 57 DNA fragments were amplified respectively by PCR. The amplified DNA fragments contain a total of 416 different SNP sites which were distributed over 24.3 kb region of the A4GALT gene including 7.0 kb of the 5' promoter region, exon 1 (74 bp), and 17.3 kb of the 5' part of intron 1. The nucleotides at each SNP over the eight samples were determined and the results are shown in Table 2. These show that 11 SNP sites of 8 subjects exhibited an association with the $P_1/P_2$ phenotype. These 11 SNPs are distributed from the +1.3 kb to +11.5 kb region in the intron 1 of the A4GALT gene, and they are denoted as SNP1 to SNP11 from 5' to 3'.

TABLE 2

SNPs in the A4GALT gene that show an association with the $P_1/P_2$ blood group phenotypes in the pilot investigation

|  |  | SNP1 | SNP2 | SNP3 | SNP4 | SNP5 | SNP6 |
|---|---|---|---|---|---|---|---|
| Location[a] |  | +1352 | +2326 | +2414 | +2837 | +2857 | +3084 |
| SNP ID |  | rs67162484[a] rs66781836[b] | rs8138197 | rs10713068 | rs2143919 | rs2143918 | rs5751348 |
| Nucleotide Polymorphisms[c] |  | AGAA/– | C/T | C/– | C/G | T/G | G/T |
| Phenotype | Sample | Genotype[c] |  |  |  |  |  |
| $P_1$ | M8 | +/+ | C/C | C/C | C/C | T/T | G/G |
|  | M5 | +/+ | C/C | C/C | C/C | T/T | G/G |
|  | M33 | +/– | C/T | C/– | C/G | T/G | G/T |
|  | HSC | +/– | C/T | C/– | C/G | T/G | G/T |
| $P_2$ | M12 | –/– | T/T | –/– | G/G | G/G | T/T |
|  | T9 | –/– | T/T | –/– | G/G | G/G | T/T |
|  | J1 | –/– | T/T | –/– | G/G | G/G | T/T |
|  | Y1 | –/– | T/T | –/– | G/G | G/G | T/T |

|  |  | SNP7 | SNP8 | SNP9 | SNP10 | SNP11 |
|---|---|---|---|---|---|---|
| Location[a] |  | +3443 | +5012 | +6762 | +7038 | +11507 |
| SNP ID |  | rs9623671 | rs111626860 | rs5758891 | rs8139674 | rs66463955 |
| Nucleotide Polymorphisms[c] |  | G/A | ACTCCA/– | T/C | G/T | G/– |
| Phenotype | Sample | Genotype[c] |  |  |  |  |
| $P_1$ | M8 | G/G | +/+ | T/T | G/G | G/G |
|  | M5 | G/G | +/+ | T/T | G/G | G/G |
|  | M33 | G/A | +/– | T/C | G/T | G/– |
|  | HSC | G/A | +/– | T/C | G/T | G/– |
| $P_2$ | M12 | A/A | –/– | C/C | T/T | –/– |
|  | T9 | A/A | –/– | C/C | T/T | –/– |
|  | J1 | A/A | –/– | C/C | T/T | –/– |
|  | Y1 | A/A | –/– | C/C | T/T | –/– |

[a]Transcription initiation nucleotide of A4GALT exon 1 (74 bp) of RefSeq Transcript NM_017436.4 in the NCBI database as +1
[b]SNPs rs67162484 and rs66781836 yield identical sequence polymorphisms.
[c]"+" and "–" indicate the presence and the absence of the nucleotide(s), respectively.

2) SNPs Rs2143918 and Rs5751348 Show a Definite Association with the $P_1/P_2$ Phenotypes Across Different Ethnic Populations.

Figure 1:
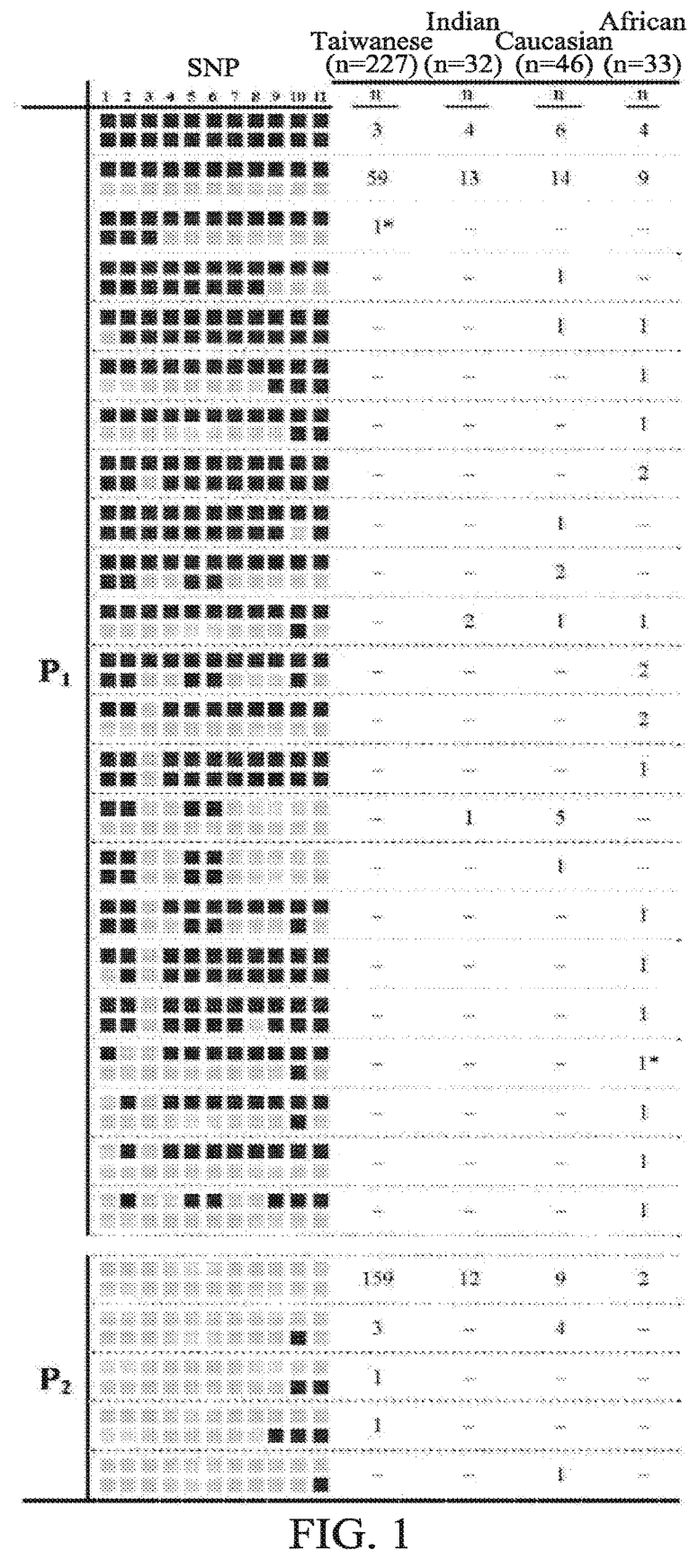

In order to verify the association of these 11 SNPs (SNP1 to SNP11) and the phenotypes of $P_1/P_2$ phenotypes, a large scale association study using various ethnic populations was carried out There were 227 Taiwanese (including 8 subjects analyzed in the previous pilot study), 32 Indians, 46 Caucasians and 33 Africans (Black) enrolled in this study. The $P_1/P_2$ phenotypes and the genotypes at SNP1 to SNP11 of these 338 subjects were determined. The distributions of the genotypes at the 11 SNPs in the $P_1$ and $P_2$ individuals of each population are shown in Table 3. The haplotypes of the 11 SNPs in the 4 populations were reconstructed and the most likely haplotype was assigned for each subject using PHASE program (version 2.1). FIG. 1 shows the distribution of the most likely haplotype pairs in the $P_1$ and $P_2$ subjects among each ethnic population.

The two haplotypes identified by using 8 Taiwanese in the pilot study were found to be major haplotypes present in the wider study and were also associated with the $P_1$ and $P_2$ phenotypes across all four populations. In addition to the two haplotypes found in the four populations, haplotypes with recombination between the 11 SNPs were identified and were found to be more frequent in Caucasians and Africans than in Taiwanese and Indians. The correlation of SNP1, SNP3, SNP4, and SNP7 to SNP11 could be easily excluded while multiple cases distributed across the different ethnic populations were identified as recombinant haplotypes between these SNPs, as shown in Table 3 and FIG. 1. Thus, it creates inconsistencies in the genotype-phenotype correlation observed across the majority of other enrolled subjects.

Among the 338 enrolled subjects, only one subject ($P_1$ Africans, denoted as ** in Table 3 and * in FIG. 1) showed the genotype-phenotype inconsistency of SNP rs8138197. In the previous analysis for the $P_1$ and $P_2$ phenotype from 208 Swedish subjects, there was one case found the genotype-phenotype inconsistency of SNP rs8138197. In addition to such $P_1$ African case, a $P_1$ Taiwanese (denoted as * in FIG. 1) labeled as M3 family was pointed out as having an allele which is involved recombination between SNP3 and SNP4. As shown in FIG. 2, the M3 family was then enrolled to perform the pedigree analysis and the recombinant allele identified in M3 was found to be present in M3's father and brother who were labeled with the $P_2$ phenotype. The results obtained from this pedigree analysis suggest that SNP2 (i.e. rs8138197) is nor involved in defining the $P_1$ and $P_2$ phenotypes.

When the above results were taken together, the SNPs that show definite association with the $P_1/P_2$ phenotypes could be narrowed down to two, namely SNP5 (rs2143918) and SNP6 (rs5751348), using this pilot study across different ethnic populations. The genotypes at the SNPs distributed along the +1.3 kb through +3.7 kb region of the A4GALT gene, which encompasses the SNP1 to SNP7 sites, of the enrolled 338 subjects were thoroughly examined, and no other SNP was found an association with the $P_1$ and $P_2$ phenotypes. The genotypes at SNPs rs2143918 and rs5751348 were consistently associated with the $P_1$ and $P_2$ phenotypic polymorphisms while 338 subjects across the four ethnic populations have considerable genetic distances.

TABLE 3

SNPs associated with the $P_1/P_2$ blood group phenotypes and distributions of the SNP genotypes in the $P_1$ and $P_2$ subjects of various ethnic populations

| | | SNP1 | | | SNP2 | | | SNP3 | | | SNP4 | | | SNP5 | | | SNP6 | | |
|---|---|---|---|---|---|---|---|---|---|---|---|---|---|---|---|---|---|---|---|
| Location[a] | | +1352 | | | +2326 | | | +2414 | | | +2837 | | | +2857 | | | +3084 | | |
| SNP ID | | rs67162484[b] rs66781836[b] | | | rs8138197 | | | rs10713068 | | | rs2143919 | | | rs2143918 | | | rs5751348 | | |
| Nucleotide Polymorphisms[c] | | AGAA (■)/—(□) | | | C (■)/T (□) | | | C (■)/—(□) | | | C (■)/G (□) | | | T (■)/G (□) | | | G (■)/T (□) | | |
| Genotypes[c] | | ■/■ | ■/□ | □/□ | ■/■ | ■/□ | □/□ | ■/■ | ■/□ | □/□ | ■/■ | ■/□ | □/□ | ■/■ | ■/□ | □/□ | ■/■ | ■/□ | □/□ |
| Taiwanese | $P_1$ (n = 63) | 5 | 58 | 0 | 5 | 58 | 0 | 5 | 58 | 0 | 4 | 59 | 0 | 4 | 59 | 0 | 4 | 59 | 0 |
| | $P_2$ (n = 164) | 0 | 0 | 164 | 0 | 0 | 164 | 0 | 0 | 164 | 0 | 0 | 164 | 0 | 0 | 164 | 0 | 0 | 164 |
| Indian | $P_1$ (n = 20) | 4 | 16 | 0 | 4 | 16 | 0 | 4 | 15 | 1 | 4 | 15 | 1 | 4 | 16 | 0 | 4 | 16 | 0 |
| | $P_2$ (n = 12) | 0 | 0 | 12 | 0 | 0 | 12 | 0 | 0 | 12 | 0 | 0 | 12 | 0 | 0 | 12 | 0 | 0 | 12 |
| Caucasian | $P_1$ (n = 32) | 11 | 21 | 0 | 12 | 20 | 0 | 9 | 17 | 6 | 9 | 17 | 6 | 12 | 20 | 0 | 12 | 20 | 0 |
| | $P_2$ (n = 14) | 0 | 0 | 14 | 0 | 0 | 14 | 0 | 0 | 14 | 0 | 0 | 14 | 0 | 0 | 14 | 0 | 0 | 14 |
| African[d] | $P_1$ (n = 31) | 11 | 17 | 3 | 13 | 17 | 1* | 5 | 16 | 10 | 10 | 20 | 1 | 13 | 18 | 0 | 13 | 18 | 0 |
| | $P_2$ (n = 2) | 0 | 0 | 2 | 0 | 0 | 2 | 0 | 0 | 2 | 0 | 0 | 2 | 0 | 0 | 2 | 0 | 0 | 2 |
| Swedish[e] | $P_1$ (n = 151) | | | | 57 | 93 | 1 | | | | | | | | | | | | |
| | $P_2$ (n = 57) | | | | 0 | 0 | 57 | | | | | | | | | | | | |

| | | SNP7 | | | SNP8 | | | SNP9 | | | SNP10 | | | SNP11 | | |
|---|---|---|---|---|---|---|---|---|---|---|---|---|---|---|---|---|
| Location[a] | | +3443 | | | +5012 | | | +6762 | | | +7038 | | | +11507 | | |
| SNP ID | | rs9623671 | | | rs111626860 | | | rs5758891 | | | rs8139674 | | | rs66463955 | | |
| Nucleotide Polymorphisms[c] | | G (■)/A (□) | | | ACTCCA (■)/—(□) | | | T (■)/C (□) | | | G (■)/T (□) | | | G (■)/—(□) | | |
| Genotypes[c] | | ■/■ | ■/□ | □/□ | ■/■ | ■/□ | □/□ | ■/■ | ■/□ | □/□ | ■/■ | ■/□ | □/□ | ■/■ | ■/□ | □/□ |
| Taiwanese | $P_1$ (n = 63) | 4 | 59 | 0 | 4 | 59 | 0 | 4 | 59 | 0 | 4 | 59 | 0 | 4 | 59 | 0 |
| | $P_2$ (n = 164) | 0 | 0 | 164 | 0 | 0 | 164 | 0 | 1 | 163 | 0 | 5 | 159 | 0 | 2 | 162 |
| Indian | $P_1$ (n = 20) | 4 | 15 | 1 | 4 | 15 | 1 | 4 | 15 | 1 | 6 | 13 | 1 | 4 | 15 | 1 |
| | $P_2$ (n = 12) | 0 | 0 | 12 | 0 | 0 | 12 | 0 | 0 | 12 | 0 | 0 | 12 | 0 | 0 | 12 |
| Caucasian | $P_1$ (n = 32) | 9 | 17 | 6 | 9 | 17 | 6 | 8 | 18 | 6 | 8 | 20 | 6 | 8 | 18 | 6 |
| | $P_2$ (n = 14) | 0 | 0 | 14 | 0 | 0 | 14 | 0 | 0 | 14 | 0 | 2 | 10 | 0 | 1 | 13 |
| African[d] | $P_1$ (n = 31) | 10 | 20 | 1 | 9 | 21 | 1 | 11 | 20 | 0 | 18 | 13 | 0 | 12 | 19 | 0 |
| | $P_2$ (n = 2) | 0 | 0 | 2 | 0 | 0 | 2 | 0 | 0 | 2 | 0 | 0 | 2 | 0 | 0 | 2 |
| Swedish[e] | $P_1$ (n = 151) | | | | | | | | | | | | | | | |
| | $P_2$ (n = 57) | | | | | | | | | | | | | | | |

The numbers of the individuals that show genotype-phenotype inconsistency compared to the majority of others are typed in red.
[a]Transcription initiation nucleotide of A4GALT exon 1 (74 bp) of RefSeq Transcript NM_017436.4 in the NCBI database as +1
[b]SNPs rs67162484 and rs66781836 yield identical sequence polymorphisms.
[c]The two different nucleotide genotypes at each SNP are denoted by ■ and □.
[d]An asterisk indicates a $P_1$ African who shows a genotype-phenotype discrepancy at SNP2.
[e]Ref. 28. The association dataset for the other SNPs in this population is not available.

By a pilot investigation and stepwise SNP screening analysis in A4GALT gene followed by an association study using four ethnic populations, the present invention confirms that SNPs rs2143918 and rs5751348 are correlated with the P1 and P2 blood type. Accordingly, the T/T and T/G genotypes at the SNP rs2143918 are associated with $P_1$ phenotype while the G/G genotype at the SNP rs2143918 is associated with $P_2$ phenotype. The G/G and G/T genotypes at the SNP rs5751348 are associated with $P_1$ phenotype while the T/T genotype at the SNP rs5751348 is associated with $P_2$ phenotype.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claim.

What is claimed is:

1. A method for determining whether a human subject has a $P_1$ or $P_2$ blood type, comprising:
   a) obtaining a biological sample from a human subject;
   b) purifying genomic DNA from the biological sample;
   c) providing a reaction mixture comprising the genomic DNA, a primer pair, a DNA polymerase, and dNTPs, wherein said primer pair comprises a first primer consisting of SEQ ID NO: 3 or the complement thereof and a second primer consisting of SEQ ID NO: 4 or the complement thereof;
   d) exposing the reaction mixture to amplification conditions to produce an amplified DNA fragment;
   e) sequencing the amplified DNA fragment to detect the genotype at SNP rs5751348;
   f) determining that the human subject has the $P_1$ blood type when the G/G or G/T genotype is detected at SNP rs5751348 or determining that the human subject has the $P_2$ blood type when the T/T genotype is detected at SNP rs5751348.

2. The method of claim 1, wherein the biological sample is blood or saliva.

* * * * *